US009782370B2

(12) United States Patent
Yang et al.

(10) Patent No.: US 9,782,370 B2
(45) Date of Patent: Oct. 10, 2017

(54) PHARMACEUTICAL COMPOSITIONS OF BENZENESULFONAMIDE DERIVATIVES FOR TREATMENT OF ADENOID CYSTIC CARCINOMA

(71) Applicant: GONGWIN BIOPHARM HOLDINGS CO., LTD., Grand Cayman (KY)

(72) Inventors: Chuan-Ching Yang, Grand Cayman (KY); Nanshan Zhong, Grand Cayman (KY); Mao-Yuan Lin, Grand Cayman (KY); Chi-Chiang Tu, Grand Cayman (KY); Kun-Hung Chen, Grand Cayman (KY); Chia-Yen Hsiao, Grand Cayman (KY)

(73) Assignee: Gongwin Biopharm Holdings Co., Ltd., Grand Cayman (KY)

( * ) Notice: Subject to any disclaimer, the term of this patent is extended or adjusted under 35 U.S.C. 154(b) by 0 days.

(21) Appl. No.: 15/387,221

(22) Filed: Dec. 21, 2016

(65) Prior Publication Data

US 2017/0172951 A1    Jun. 22, 2017

Related U.S. Application Data

(60) Provisional application No. 62/270,555, filed on Dec. 21, 2015.

(51) Int. Cl.
| | | |
|---|---|---|
| *A61K 31/18* | (2006.01) | |
| *A61K 47/10* | (2017.01) | |
| *A61K 9/00* | (2006.01) | |
| *A61K 47/20* | (2006.01) | |
| *A61K 47/12* | (2006.01) | |

(52) U.S. Cl.
CPC ............ *A61K 31/18* (2013.01); *A61K 9/0019* (2013.01); *A61K 47/10* (2013.01); *A61K 47/12* (2013.01); *A61K 47/20* (2013.01)

(58) Field of Classification Search
None
See application file for complete search history.

(56) References Cited

PUBLICATIONS

Gao et al., Journal of Thoracic Disease (2013) 5(4), pp. 472-483.*
Allen, "Malignant Tracheal Tumors", Mayo Clinic Proceedings, 1993, 68: 680-684.
Bittner, et al., "Treatment of locally advanced adenoid cystic carcinoma of the trachea with neutron radiotherapy", International Journal of Radiation Oncology Biology Physics, Oct. 1, 2008, 72: 410-414.
Calzada, et al., "Adenoid cystic carcinoma of the airway: a 30-year review at one institution", American Journal Otolaryngology, 2012, 33:226-231.
El Marjany, et al., "Primary adenoid cystic carcinoma of the trachea: a report of two cases and literature review", Pan African Medical Journal, 2014, 19:32.
Gaissert, et al., "Long-Term Survival After Resection of Primary Adenoid Cystic and Squamous Cell Carcinoma of the Trachea and Carina", Ann Thorac Surg 2004;78:1889-97.
Grillo, "Management of Tracheal Tumors", Am J Surgery 1982, 143:697-699.
Grillo, et al., "Primary Tracheal Tumors: Treatment and Results", Ann Thorac Surg. Jan. 1990; 49:69-77.
Hajdu, et al., "Carcinoma of the Trachea, Clinicopathologic Study of 41 Cases", Cancer, Jun. 1970, 25:1448-1456.
Jo, et al., "Hemoptysis and Dyspnea in a 67-Year-Old Man With a Normal Chest Radiograph", Chest. 1999;116:803-807.
Kanematsu, et al., "Treatment Outcome of Resected and Nonresected Primary Adenoid Cystic Carcinoma of the Lung", Ann Thorac Cardiovasc Surg. Apr. 2002, 8:74-7.
Keam, et al., "Phase 2 Study of Dovitinib in Patients With Metastatic or Unresectable Adenoid Cystic Carcinoma", Cancer, Aug. 1, 2015, 121:2612-2617.
Le Pechoux, et al., "Cylindromes thoraciques Thoracic Adenoid cystic carcinomas", Cancer/Radiotherapie 2005, 33:226-231.
Maziak, et al., "Adenoid cystic carcinoma of the airway: Thirty-two-year experience", J Thorac Cardiovasc Surg. Dec. 1996;112: 1522-31.
Mitchell, et al., "Bronchoscopic Management of Malignant Airway Obstruction", Advances in Therapy, 2014, 31:512-538.
Moran, et al., "Primary Adenois Cystic Carcinoma of the Lung", Cancer, Mar. 1, vol. 73, No. 5 (Mar. 1, 1994).
Outwater, "Imaging of the Liver for Hepatocellular Cancer", vol. 17, No. 2, Apr. 2010.
Regnard, et al., "Results and prognostic factors in resections of primary tracheal tumors: a multicenter retrospective study", J Thorac Cardiovasc Surg. Apr. 1996, 111:808-913.
Solda, et al., "Tracheal Cancer: A comprehensive Review", Annals of Otolaryngology and Rhinology, 2015, 3:1079.
Yang, et al., "Adenoid Cystic Carcinoma of the Trachea: A Report of Seven Cases and Literature Review", Chang Gung Med. J. vol. 28 No. 5 (May 2005).

* cited by examiner

*Primary Examiner* — Brian J Davis
(74) *Attorney, Agent, or Firm* — Kramer Amado, P.C.

(57) ABSTRACT

Provided is a method for treating adenoid cystic carcinoma by using a pharmaceutical composition including benzenesulfonamide derivatives and pharmaceutically acceptable carriers.

20 Claims, 5 Drawing Sheets

PHARMACEUTICAL COMPOSITIONS OF BENZENESULFONAMIDE DERIVATIVES FOR TREATMENT OF ADENOID CYSTIC CARCINOMA

BACKGROUND

Technical Field

The present disclosure relates to a method for treating adenoid cystic carcinoma (ACC), especially tracheal adenoid cystic carcinoma (TACC), in a subject by a pharmaceutical composition containing the benzenesulfonamide derivatives.

Description of Related Art

Adenoid cystic carcinoma (ACC) is a rare form of adenocarcinoma, which is a broad term describing any cancer that begins in glandular tissues. ACC most commonly occurs in the salivary glands, but may also arise in a wide range of other locations (exocrine glands) including, for example, the breast, lacrimal gland, and in the cervix, vulva, skin (including ceruminal glands of the ear), prostate, and tracheobronchial tree. Due to the distinctive morphology and histogenesis, ACC are completely different from other tumors which are mainly consisted of squamous cell carcinomas (SCC) in clinical presentation, clinical outcome, treatment, and response to treatment.

Ninety percent of tracheal cancer in adults is malignant. Among malignant tracheal tumor, squamous cell carcinoma represents the most frequent histology (44%-63%), while tracheal adenoid cystic carcinoma (TACC) accounts for 7%-16% of the cases (Ann Otolaryngol Rhinol 2015, 3:1079). TACC originates from the submucosal glands of the airway, and ultimately one-third of TACC cause malignant airway obstruction (MAO) with associated symptoms (Adv Ther 2014, 31:512-538), which is a potential life-threatening condition.

Primary cancer of the trachea is a relatively rare and accounts for only 0.1%-0.4% of all newly diagnosed respiratory tract cancers, which corresponds to 2.6 new cases per 1,000,000 individuals annually worldwide, and less than 2 per million persons per year in the United States (equivalent to 641 persons per year in 2015's US population) (J Thorac Cardiovasc Surg 1996, 112:1522-1531). It is shown that the prevalence of TACC is less than 100 per year and therefore being designated as a rare disease.

According to previous epidemiology and health statistics, smoking remains the major risk factor of SCC, but it does not seem to affect the incidence of TACC. The delay in diagnosis of TACC often occurs because the pulmonary fields remain normal on a chest radiograph (Chest 1999, 116:803-807); and patients with TACC usually present with symptoms such as coughing, wheezing and dyspnea and are often treated for asthma for months to years before being correctly diagnosed (Mayo Clin Proc 1993, 68: 680-684).

TACC is generally considered to be a low grade malignancy, but it tends to metastasize to distant sites and often recurs after a long interval (Chang Gung Med J 2005, 28:357-363). The survival is frequently less than 2 years with distal metastasis (Cancer 1994, 73:1390-1397). ACC spreads most commonly by direct extension, submucosal or perineural invasion, or hematogenous metastasis. Pulmonary metastasis is the most common, and metastasis to the brain, bone, liver, kidney, abdomen, and hearts have been reported (J Thorac Cardiovasc Surg 1996, 111:808-913; Am J Surgery 1982, 143:697-699; Cancer 1970, 25:1448-1456).

In the early stage of the disease, primary treatment includes surgery with optional postoperative radiotherapy (RT). With the combined therapy, the 5-year overall survival (OS) rate reaches up to 52% in TACC (Int J Radiat Oncol Biol Phys 2008, 72:410-414; Ann Thorac Surg 1990, 49:69-77). However, resection is often difficult if there is invasion of adjacent critical tissues especially in patients with distal tracheal involvement (Am J Otolaryngol 2012, 33:226-231; Cancer/Radiotherapie 2005, 33:226-231), or tumors are too large to permit surgery. The complete resection rate is reported to 42%-57% (Ann Thorac Cardiovasc Surg 2002, 8:74-77). Negative surgical margins are difficult to obtain because of the relative inability to resect more than 6 cm of the trachea, and thus TACC are prone to local recurrence (Am J Otolaryngol 2012, 33:226-231).

Radiotherapy (RT) is used as the primary modality in unresectable TACC. However, TACC exhibits a limited response to chemotherapy and RT (Ann Otolaryngol Rhinol 2015, 3:1079). Compared to 52% of 5-year survival rate of resected patients, the unresectable patients (subjected to only radiotherapy) have a lower survival rate (33% in 5 years) (Ann Thorac Surg 2004, 78:1889-1897).

In general, current therapies do not possess sufficient tumor/normal tissue selectivity, and thus the efficacy is limited in infiltrative lesions commonly seen in TACC (Pan Afr Med J 2014, 19:32). On the other hand, the FDA-designated orphan drug for adenoid cystic carcinoma, Dovitinib, a multi-targeted kinase inhibitor, shows modest anti-tumor activity in the treatment of TACC. However, a complete treatment cycle takes 8 weeks, and nearly 94% of the patients in the clinical study had stable disease outcome (Cancer 2015, 121:2612-2617), which would hardly be satisfactory in the life-threatening airway obstruction condition. Therefore, there is a need in TACC patients for a therapy to provide tumor clearance as efficient as physical therapy/resection, and as specific as targeted therapy.

Toluene sulfonamide is known as an effective anti-fungal agent and used to treat plant and animal (e.g., human) tissues infected with a fungus. U.S. Pat. No. 5,891,454 and U.S. Pat. No. 6,727,287 both disclose a sulfonamide-containing composition that exhibits anti-cancer and anti-tumor necrotizing activity. However, there is still a need in the art for providing an injectable composition which provides sustained concentration of toluene sulfonamide and long acting effects for treating cancers.

SUMMARY

In one embodiment of the present disclosure, a pharmaceutical composition for treating cancer is provided. The pharmaceutical composition comprises a benzenesulfonamide derivative or a pharmaceutically acceptable salt thereof, and a pharmaceutically acceptable carrier.

The pharmaceutical composition of the present disclosure has a viscosity of from 20 to 200 cP. In one embodiment of the present disclosure, the pharmaceutical composition has a viscosity of from 40 to 60 cP, such as from 47.2 to 48.4 cP.

In one embodiment of the present disclosure, the benzenesulfonamide derivative in the pharmaceutical composition may be represented by formula (I):

or a pharmaceutically acceptable salt thereof, wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring, and wherein the alkyl, alkoxy, cycloalkyl, cycloheteroalkyl group and the ring are unsubstituted or substituted with one or more substituents. In one embodiment of the present disclosure, the substituent may be selected from the group consisting of phenyl, halo, oxo, ether, hydroxyl, carboxyl, amino, sulfo and sulfonamide group.

In one embodiment of the present disclosure, the benzenesulfonamide derivative or the pharmaceutically acceptable salt thereof may be at least one selected from the group consisting of para-toluene sulfonamide (p-TSA), ortho-toluene sulfonamide, meta-toluene sulfonamide, N-ethyl ortho-toluene sulfonamide, N-ethyl para-toluene sulfonamide, N-cyclohexyl para-toluene sulfonamide, -continued In one embodiment of the present disclosure, the pharmaceutically acceptable carrier may be selected from the group consisting of polyethylene glycol (PEG), alkylene glycol, sebacic acid, dimethyl sulfoxide (DMSO), alcohol and a combination thereof. In another embodiment of the present disclosure, the alkylene glycol may be at least one of 2-ethyl-1,3-hexandiol and propanediol.

In one embodiment of the present disclosure, the pharmaceutical composition comprises PEG-400, 2-ethyl-1,3-hexandiol, propanediol, sebacic acid, and DMSO.

In one embodiment of the present disclosure, the benzenesulfonamide derivative may be present in an amount of from 10% to 50% by weight. In another embodiment of the present disclosure, the benzenesulfonamide derivative may be present in an amount of from 20% to 40% by weight.

In one embodiment of the present disclosure, the pharmaceutical composition comprises at least one of 20% to 50% by weight of PEG, 5% to 15% by weight of propanediol, 1% to 5% by weight of sebacic acid, 10% to 20% by weight of 2-ethyl-1,3-hexanediol, 5% to 10% by weight of dimethyl sulfoxide and more than 0% to 30% by weight of anhydrous ethanol.

In one embodiment of the present disclosure, the pharmaceutical composition comprises para-toluene sulfonamide (p-TSA) in an amount of 33% by weight, the PEG-400 in an amount of 35.5% by weight, the 2-ethyl-1,3-hexandiol in an amount of 16.4% by weight, the propanediol in an amount of 8.2% by weight, the sebacic acid in an amount of 3.7% by weight, and the DMSO in an amount of 6.7% by weight.

In one embodiment of the present disclosure, the pharmaceutical composition may be in a form suitable for injection.

In another embodiment of the present disclosure, the method for treating adenoid cystic carcinoma is provided. The method comprises administering a therapeutically effective amount of the pharmaceutical composition comprising a benzenesulfonamide derivative or a pharmaceutically acceptable salt thereof, and a pharmaceutically acceptable carrier to a subject in need thereof.

In one embodiment of the present disclosure, the pharmaceutical composition may be administered to the subject intratumorally, intravenously, subcutaneously, intradermally, intrathecally, intraperitoneally, intramuscularly, or intrapleuraly.

In one embodiment of the present disclosure, the method is for treating adenoid cystic carcinoma which may be tracheal adenoid cystic carcinoma.

DETAILED DESCRIPTION

The following examples are used to exemplify the present disclosure. A person of ordinary skills in the art can understand the other advantages of the present disclosure, based on the disclosure of the specification of the present disclosure. The present disclosure can also be implemented or applied as described in different specific examples. It is possible to modify and or alter the examples for carrying out this disclosure without contravening its spirit and scope, for different aspects and applications.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

The present disclosure provides a pharmaceutical composition or a drug product that has a viscosity of from 20 to 200 cP. Particularly, the present disclosure provides a pharmaceutical composition containing the benzenesulfonamide derivatives or pharmaceutically acceptable salts thereof and pharmaceutically acceptable carriers that have viscosity of from 40 to 60 cP.

In an embodiment of the present disclosure, the pharmaceutical composition exhibits anti-tumor activity, and comprises the benzenesulfonamide derivatives or pharmaceutically acceptable salts thereof and the pharmaceutically acceptable carriers, wherein the benzenesulfonamide derivative is represented by formula (I)

(I)

or a pharmaceutically acceptable salt thereof, wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring.

In an embodiment of the present disclosure, the alkyl, alkoxy, cycloalkyl, cycloheteroalkyl and the ring in $R_1$ to $R_7$ are independently unsubstituted or substituted with one or more substituents. In another embodiment of the present disclosure, the substituent is selected from the group consisting of phenyl, halo, oxo, ether, hydroxyl, carboxyl, amino, sulfo and sulfonamide group.

In an embodiment of the present disclosure, the pharmaceutically acceptable carriers are chosen from polyethylene glycol (PEG), alkylene glycol, sebacic acid, dimethyl sulfoxide (DMSO), alcohol and a combination thereof. The examples of the alkylene glycol include, but are not limited to, 2-ethyl-1,3-hexandiol and propanediol. The example of the PEG includes, but is not limited to, PEG-400.

In an embodiment of the present disclosure, the benzenesulfonamide derivatives are in an amount of 10% to 50% of the composition by weight. For example, an amount of the benzenesulfonamide derivative in the pharmaceutical composition has a lower limit chosen from 10%, 15%, 20%, and 25% of the composition by weight, and an upper limit chosen from 50%, 45%, 40% and 35% of the composition by weight.

In an embodiment of the present disclosure, the pharmaceutically acceptable carriers are chosen from at least one of 20%-50% by weight of PEG, 5%-15% by weight of propanediol, 1%-5% by weight of sebacic acid, 10%-20% by weight of 2-ethyl-1,3-hexanediol, 5%-10% by weight of dimethyl sulfoxide and more than 0%-30% by weight of anhydrous ethanol.

In an embodiment of the present disclosure, the pharmaceutical composition comprises p-TSA in an amount of 33% by weight, PEG-400 in an amount of 35.5% by weight, 2-ethyl-1,3-hexandiol in an amount of 16.4% by weight, propanediol in an amount of 8.2% by weight, sebacic acid in an amount of 3.7% by weight, and DMSO in an amount of 6.7% by weight.

The present disclosure also provides a method of treating ACC or symptom due to ACC by intratumoral injection of said pharmaceutical composition. In an embodiment of the present disclosure, the ACC or the symptom due to ACC may be at least one selected from the group consisting of tracheal adenoid cystic carcinoma, and malignant airway obstruction.

In an embodiment of the present disclosure, the method comprises injecting the pharmaceutical composition into an injection site of the subject. In an embodiment of the present disclosure, the injection site is an intratumoral site which may be determinable by an ultrasonic imaging system or a bronchoscopy.

In an embodiment of the present disclosure, the benzenesulfonamide derivatives in the pharmaceutical composition may be administered to the subject in a therapeutically effective amount of from about 1000 mg to about 3300 mg per day, such as 1650 mg per day, 1980 mg per day and 2640 mg per day.

In an embodiment of the present disclosure, the pharmaceutical composition may be administered to the subject 1 to 4 times per week, such as 2 times per week and 3 times per week.

In an embodiment of the present disclosure, the pharmaceutical composition may be administered to the subject for a 1- to 3-weeks treatment period, such as 2-weeks treatment period.

In an embodiment of the present disclosure, the method further comprises monitoring at least one condition resulting from the injection by using the ultrasonic imaging system or the bronchoscopy. In an embodiment of the present disclosure, the resulting condition is diffusion condition.

In an embodiment of the present disclosure, the diffusion condition may be determinable by observing the diffusion of the pharmaceutical composition from the injection site to a peripheral site.

In an embodiment of the present disclosure, the pharmaceutical composition may be loaded in a needling instrument with an 18 G needle before administering to the subject.

The present disclosure provides a method of providing a pharmaceutical composition into a tissue, comprising injecting, by a needling instrument, the pharmaceutical composition into an injection site in a tissue, wherein the pharmaceutical composition comprises a benzenesulfonamide derivative such as p-TSA and the pharmaceutically acceptable carriers, and has a viscosity of from 20 to 200 cP. In an embodiment of the present disclosure, the pharmaceutical composition has a viscosity of from 40 to 60 cP, such as from 47.2 to 48.4 cP, and the needling instrument comprises an 18 G needle.

In an embodiment of the present disclosure, the pharmaceutical composition is injected to the subject at a rate of about 0.1 mL to 0.2 mL per second.

In an embodiment of the present disclosure, the injection of the pharmaceutical composition is monitored by an ultrasonic imaging system or a bronchoscopy.

The present disclosure also provides a method of diffusing a pharmaceutical composition in a tissue, comprising determining a tumor borderline and an intratumoral injection site by using an ultrasonic imaging system or a bronchoscopy, and injecting, by a needling instrument, a predetermined amount of a pharmaceutical composition into the intratumoral injection site.

In an embodiment of the present disclosure, the pharmaceutical composition comprises a benzenesulfonamide derivative such as p-TSA and the pharmaceutically acceptable carriers, and has a viscosity of from 20 to 200 cP. In an embodiment of the present disclosure, the pharmaceutical composition has a viscosity of from 40 to 60 cP, such as from 47.2 to 48.4 cP, and the needling instrument comprises an 18 G needle.

The present disclosure also provides a method of accumulating a pharmaceutical composition in a local tumor to generate a clinically effective outcome, comprising injecting, by a needling instrument, the pharmaceutical composition in an intratumoral injection site, wherein the pharmaceutical composition has a viscosity of from 20 to 200 cP, the intratumoral injection site is determinable by using an ultrasonic imaging system or a bronchoscopy, and the needling instrument has an 18 G needle.

In an embodiment of the present disclosure, the accumulation of the pharmaceutical composition is observable by an ultrasonic imaging system or a bronchoscopy.

The present disclosure also provides a method of monitoring a movement of a pharmaceutical composition in a tissue, comprising obtaining an image by using a transducer of an ultrasonic imaging system; determining an injection site by analyzing the image; injecting the pharmaceutical composition in the injection site; and monitoring a change in the image.

The present disclosure also provides a method of accumulating a pharmaceutical composition in a local tumor and reducing injecting difficulty, comprises injecting, by a needling instrument, the pharmaceutical composition in an intratumoral injection site, wherein the needling instrument has an 18 G needle, and the pharmaceutical composition has a viscosity of from 20 cP to 200 cP; and the intratumoral injection site is determinable by using an ultrasonic imaging system or a bronchoscopy.

In an embodiment of the present disclosure, the method further comprises elevating the visibility of the injection of the pharmaceutical composition under the ultrasonic imaging system or the bronchoscopy.

The present disclosure also provides a method of diffusing a pharmaceutical composition in a tissue of a subject to generate a clinically effective outcome. The method comprises injecting, by a needling instrument, the pharmaceutical composition in an intratumoral injection site of the tissue, wherein the needling instrument has an 18 G needle, the pharmaceutical composition has a viscosity of from 20 cP to 200 cP, and the intratumoral injection site is determinable by using an ultrasonic imaging system or a bronchoscopy.

The present disclosure further provides a method of using an ultrasound machine to identify a desirable position or regions, mainly a tumor position in an organ, and simultaneously monitor the diffusion of a pharmaceutical composition in an intratumoral injection.

The present disclosure further relates to a method of using ultrasound machine to identify a desirable position or regions, mainly the tumor position in an organ and simultaneous monitor the diffusion of a p-TSA-containing composition in an intratumoral injection.

In an embodiment of the present disclosure, the pharmaceutical composition is in a form suitable for injection. For example, the pharmaceutical composition can be formulated to be a clear, colorless, oily, sterile solution packaged in either 3- or 5-mL glass ampoule.

The following are specific embodiments further demonstrating the efficacy of the current disclosure, but not to limit the scope of the current disclosure.

EXAMPLES

The present disclosure is further described by means of the following examples. However, these examples are only illustrative of the disclosure, and in no way limits the scope and meaning of the present disclosure. Indeed, many modifications and variations of the present disclosure will be apparent to those skilled in the art upon reading this specification, and can be made without departing from its spirit and scope.

Example 1: Viscosity of Toluene Sulfonamide-Containing Pharmaceutical Composition (Samples A and B)

Two different samples were used in this example. Sample A contained 33% by weight of p-TSA, 35.5% by weight of PEG-400, 16.4% by weight of 2-ethyl-1,3-hexandiol, 8.2% by weight of propanediol, 3.7% by weight of sebacic acid, 6.7% by weight of DMSO, and 1.5% by weight of anhydrous ethanol. Sample B was a mixture of Sample A with extra anhydrous ethanol by volume at a ratio of 5 to 2 (Sample A: 99.5% Ethanol=5:2, v:v).

The samples used in this example, especially Sample A, had been shelved for about three years before the subsequent experiments, and that a person having ordinary skill in the art would understand that such data derived from the samples might deviate from the fresh equivalent solution and that certain deviation from the data should be allowable.

The viscosity of Sample A was measured in order to determine which viscosity was suitable for liver cancer, liver tumor, and/or hepatoma treatment. The model used in such study was a Brookfield Digital Viscometer, Model HADV-1. The study was performed as instructed by the Operation Instructions as indicated in the Official Manual of the Device (No. M/92-0210O604). The procedure of the study was herein briefly incorporated and described.

A 0.5 mL Sample A, and a 0.5 mL Sample B were used in the study. A spindle (CPE-40) was used as suggested to be compatible with a sample volume around 0.5 mL. The spindle was immersed in the samples respectively. The experiment was carried out under room temperature, and the speed was set at 100 RPM. Multiple times of viscosity measurement were taken. All viscosity data were recorded before and when the resulting values stabilize and converge into a stable range. As shown in Table 1, Sample A had a torque between 71.9% and 73.7%, and a viscosity of 40 to 60 cP (centipoise), or at a centralized value, 47.2 to 48.4 cP. Sample B had a torque between 28.6% and 35.5%, and a viscosity of 18.2 to 23.3 cP.

TABLE 1

|  | Sample A | Sample B |
|---|---|---|
| Torque | 71.9%-73.7% | 28.6%-35.5% |
| cP | 40-60 | 18.2-23.3 |
|  | 47.2-48.4 |  |

The present study intended to present two compositions differing in their viscosity and intended to establish the influences of different viscosity that might further affect the composition retention time, diffusion and accumulation condition when injected into tissues or organs. It was understandable to a person having ordinary skill in the art that different compositions with same preparing process, different compositions with different preparing processes, and same composition with different preparing processes might results in the same or different composition with same or different viscosity measures.

Example 2: Diffusion and Retention of Samples A and B in an Animal Model

To evaluate the influence of different composition viscosity on a living tissue or organ (ex vivo study), an animal study was carried out under proper ethical and moral standards. Particularly, the experiment intended to evaluate the condition when a medical operator is injecting a p-TSA-containing pharmaceutical composition using a needling instrument to a tissue or organ, particularly a liver, and preferably a cancerous tissue in a liver. It has already been established that ultrasound can reveal the position of hepatocellular carcinoma and can identify the tumor borderline (See Eric K. Outwater, *Imaging of the Liver for Hepatocellular Cancer,* Cancer Control. Vol. 17, No. 2, April 2010). It was intended of this experiment to examine the capability of an ultrasound device in identifying a desirable position, region, site or area in a tissue or organ for injection and simultaneously monitor the injection process, condition, requirement and results.

The experiment was carried out by trained researchers and doctors. The materials used herein were as follows: fresh pig livers stored in a portable low temperature chamber, 18 cm with 18 G needles, 18 cm with 22 G needles, 10 mL syringes, Sample A as indicated in Table 1, Sample B (Sample A: 99.5% Ethanol=5:2, v:v), anhydrous ethanol (Sigma Aldrich #32205) and Toshiba Aplio 500-S500 ultrasound machine (an ultrasonic imaging system).

The experiment was performed by the following steps.
1. Ultrasound gel was applied to parts of the pig liver surface evenly by a transducer. The transducer was then affixed at a position that allowed clear imaging and recording of a predetermined injection site which was around 1 to 2 cm under the liver surface.
2. A loaded needling instrument was pre-prepared by loading the sample of about 5 mL in an 18 cm with 18 G needle needling instrument.
3. The needle part was inserted until the tip reached the injection site. After insertion, the sample was injected into the injection site at a rate of around 0.1 to 0.2 c.c. per second. The images of the distribution, diffusion and retention status were recorded. Visibility on whether the injection was identifiable by the ultrasound imaging system and the easibility/difficulty of the injection were provided by the doctors who performed the injection. Visibility was measured on a scoring system from S1 to S5, where S1 reflected Cleary Visible while S5 reflected Invisible. Easibility/Difficulty was measured on a scoring system from A1 to A5, where A1 reflected Easy to inject while A5 reflected Uninjectable (cannot inject into the tissue).
4. After 1 mL of the sample was injected, the needle was removed and the leakage of the sample, mainly from the puncture resulted from the needle insertion, was observed and recorded immediately.
5. The samples were allowed some time to react to the tissue until it was further observed. An incision was made on the injection site so that the diffusion and distribution of the sample were observed and recorded.

Same procedures were performed by using an 18 cm with 22 G needle. The experiment therefore provided four sets of data, i.e., 18 G needle with Sample A, 18 G needle with Sample B, 22 G needle with Sample A, and 22 G needle with Sample B.

Figure 1A:
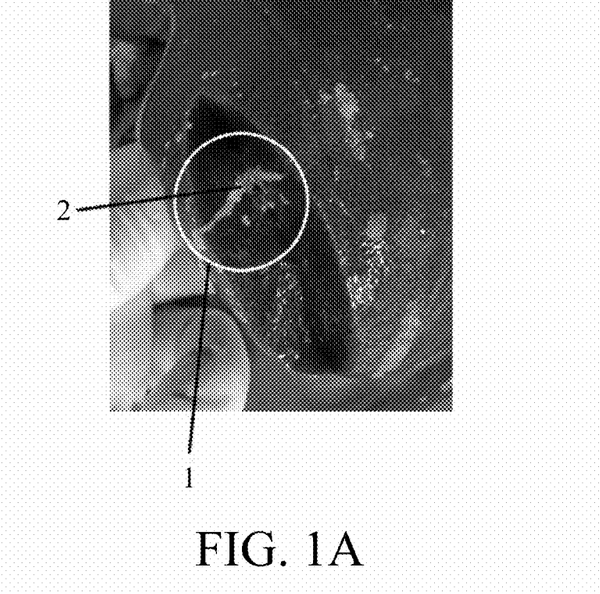
FIG. 1A shows a photo of the incised injection site after 1 mL of Sample A is injected by an 18 cm with 18 G (18 Gauge) needle needling instrument.
Figure 1B:
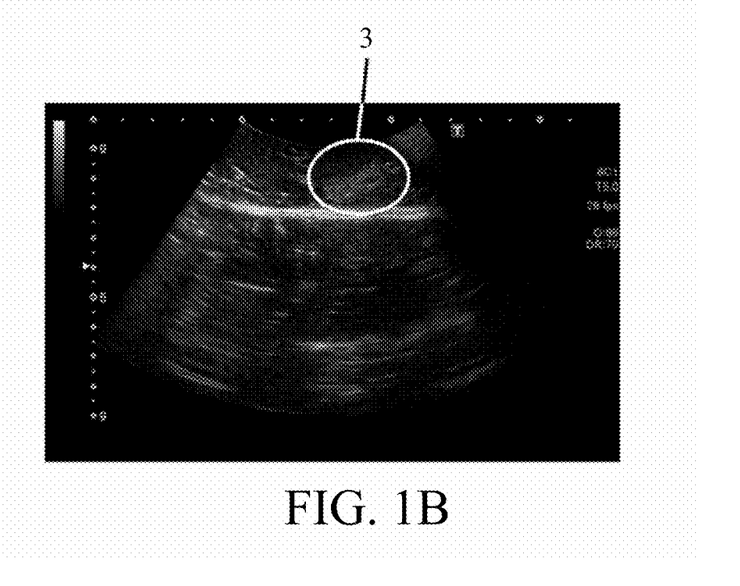
FIG. 1B shows an ultrasound image of the incised injection site after 1 mL of Sample A is injected by an 18 cm with 18 G needle needling instrument.

Referring to the results of the experiment, in both FIG. 1A and FIG. 1B, there was shown the incised injection site after 1 mL of Sample A was injected by an 18 cm with 18 G needle needling instrument. As shown in FIG. 1A, an Injection Site 1 was indicated by a circle. The Injection Site 1 revealed a faded color Portion 2 which indicated protein denaturation due to the interaction between Sample A and the tissue. Such protein denaturation was one of the clinical effects if the composition is injected into a tumor, which damages and necrotizes the cells. In FIG. 1B, Diffusion Pattern 3 was indicated by a circle. Diffusion Pattern 3 showed that the sample was confined and accumulated at a region. As provided by the doctors, the level of easibility/difficulty was A3, and the level of Visibility was S2. There was no identifiable leakage after the needle was removed from the tissue under this condition.

Figure 2A:
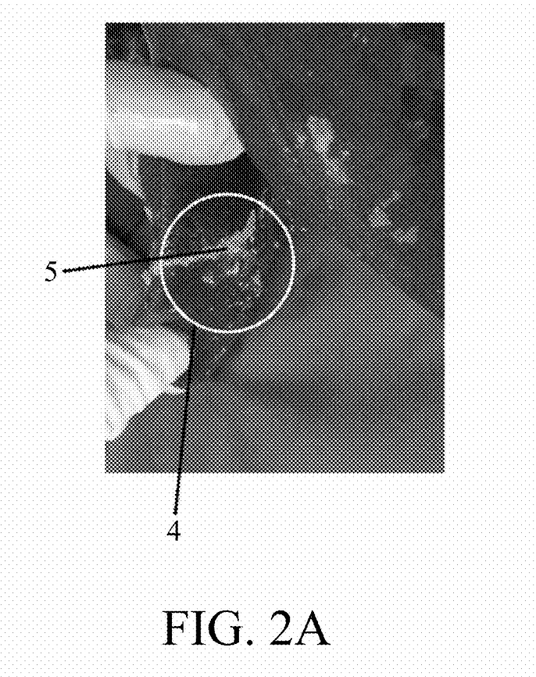
FIG. 2A shows a photo of the incised injection site after 1 mL of Sample A is injected by an 18 cm with 22 G needle needling instrument.
Figure 2B:
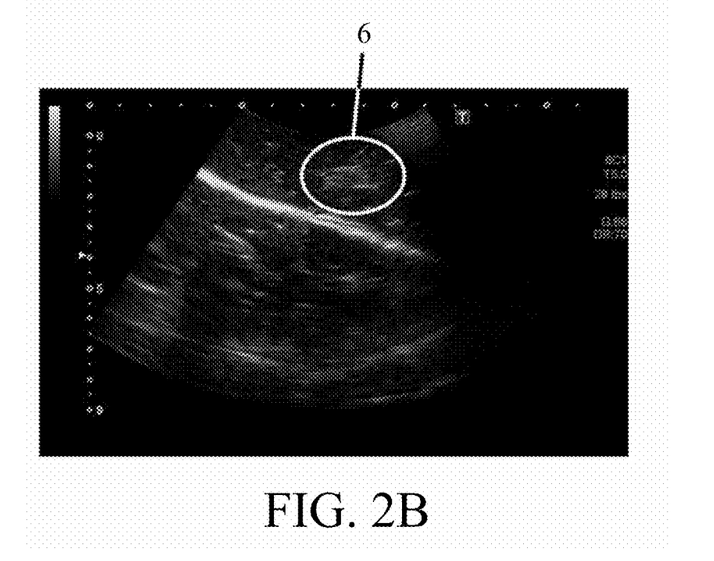
FIG. 2B shows an ultrasound image of the incised injection site after 1 mL of Sample A is injected by an 18 cm with 22 G needle needling instrument.

Further referring to FIG. 2A and FIG. 2B, there was shown the incised injection site after 1 mL of Sample A was injected by an 18 cm with 22 G needle needling instrument. As shown in FIG. 2A, an Injection Site 4 was indicated by a circle. The Injection Site 4 revealed a faded color Portion 5 which indicated protein denaturation due to the interaction between Sample A and the tissue. In FIG. 2B, Diffusion Pattern 6 was indicated by a circle. Diffusion Pattern 6 shows that the sample was confined and accumulated at a region. As provided by the doctors, the level of easibility/difficulty was A4, and the level of Visibility was S3, which suggest that it was harder to use an 22 G needle to inject than a 18 G needle and less visible than a 18 G needle injection under ultrasonic imaging. There was only minor leakage, in the experiment a small drop, which at first was identifiable but then was absorbed back into the tissue.

Figure 3A:
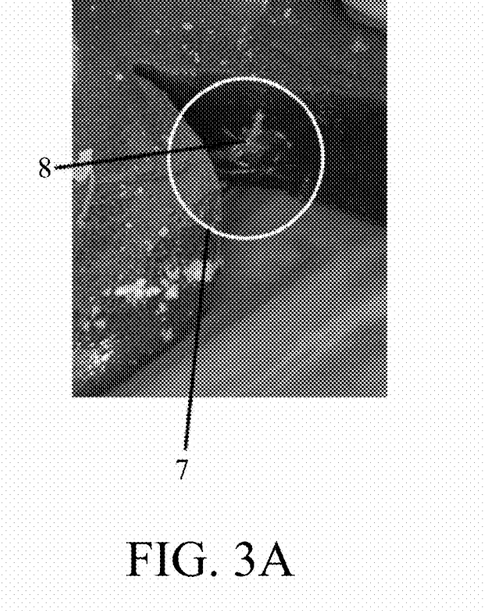
FIG. 3A shows a photo of the incised injection site after 1 mL of Sample B is injected by an 18 cm with 18 G needle needling instrument.
Figure 3B:
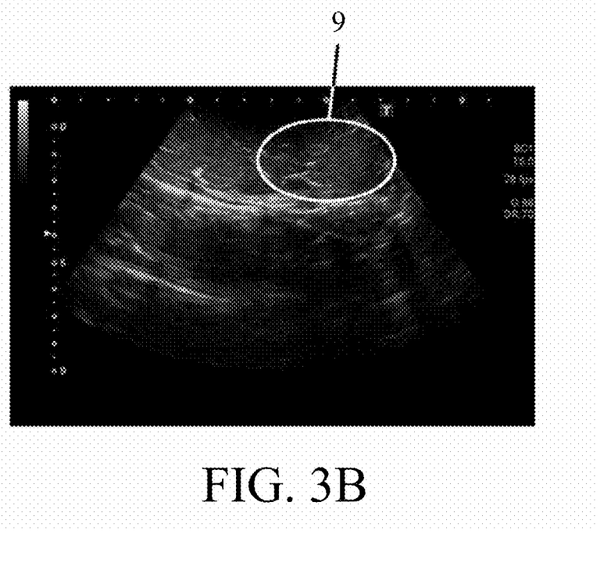
FIG. 3B shows an ultrasound image of the incised injection site after 1 mL of Sample B is injected by an 18 cm with 18 G needle needling instrument.

Referring to FIG. 3A and FIG. 3B there was shown the incised injection site after 1 mL of Sample B was injected by an 18 cm with 18 G needle needling instrument. As shown in FIG. 3A, an Injection Site 7 was indicated by a circle. The Injection Site 7 revealed a faded color Portion 8 which indicated protein denaturation due to the interaction between Sample B and the tissue. Portion 8 also revealed that the color faded portion had a less defined border between unreached tissues and the interacted tissues, which suggested a stronger diffusion of the sample into the tissue. In FIG. 3B, Diffusion Pattern 9 was indicated by a circle. Diffusion Pattern 9 showed that the sample was not well confined and a border between unreached tissue and interacted tissue was not clearly identifiable. As provided by the doctors, the level of easibility/difficulty was A2 to A3, and the level of Visibility was 51. The visibility difference might result from the different compositions. Under ultrasonic imaging, Sample B had a higher visibility and an increased diffusion pattern in the experiment than in Sample A. Such diffusion phenomenon leaded to inability to constrain, limit and confine the sample in a desirable region. Leakage of the sample from the puncture caused by the needle was barely identifiable.

Figure 4:
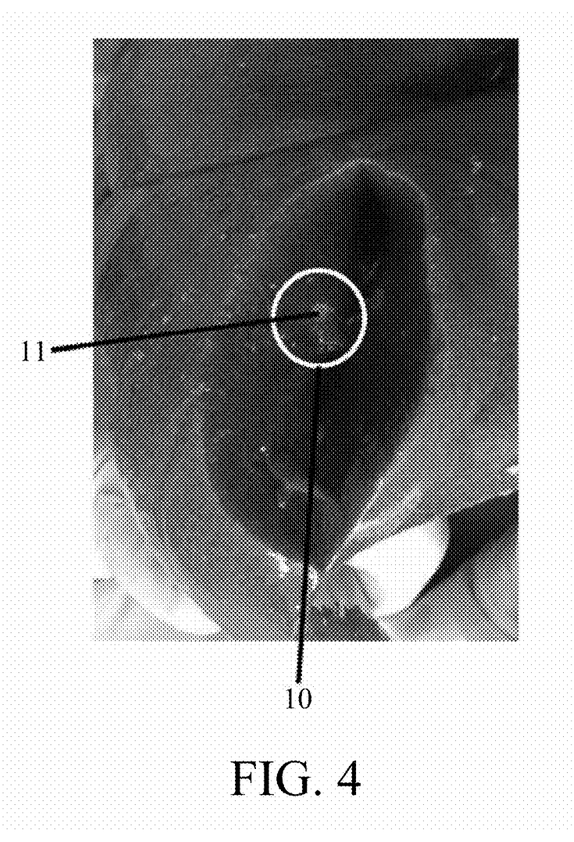
FIG. 4 shows a photo of the incised injection site after 1 mL of Sample B is injected by an 18 cm with 22 G needle needling instrument.

Referring now to FIG. 4, there was shown the incised injection site after 1 mL of Sample B was injected by an 18 cm with 22 G needle needling instrument. As shown in FIG. 4, an Injection Site 7 was indicated by a circle. The Injection Site 10 revealed a faded color Portion 11 which indicated protein denaturation due to the interaction between Sample B and the tissue. As provided by the doctors, the level of easibility/difficulty was A4, and the level of Visibility was S4. While Sample B is being injected, the doctor commented that it is difficult to push the sample into the tissue and it takes longer than previous experiments and thus provide more time for the sample to diffuse into the tissue. A wilder diffusion pattern also reflected the poor visibility under ultrasonic imaging. In addition, during the injection, a certain amount of the sample was spread onto the surface due to a burst out caused by over-pressurizing the syringe. Again, the diffusion phenomenon leaded to inability to constrain, limit and confine the sample in a desirable region.

According to the doctor, the combination of 18 cm 18 G needling instrument with Sample A was a preferred treatment setting in an intra-tissue injection.

The diffusion and retention experiment results were compiled in Table 2.

TABLE 2

|  | Sample A + 18G | Sample A + 22G | Sample B + 18G | Sample B + 22G |
|---|---|---|---|---|
| Visibility | S2 | S3 | S1 | S4 |
| Easibility/Difficulty | A3 | A4 | A2-A3 | A4 |
| Diffusion Pattern | Less diffusion | Less diffusion | Diffused | Diffused |
| Leakage | Not observed | Limited leakage | Not observed | Leaked due to dislodged needle |

Combining data from viscosity measure of the samples and the data from the liver injection, the present disclosure demonstrates that in liver tissue, there is a desirable pharmaceutical composition viscosity for a desirable diffusion pattern or confinement condition or accumulation condition, which leads to desirable clinical effects on the injection site. A desirable intratumoral injection of anticancer agents depends on both the potency and efficacy exerted by the anticancer agents and the distribution of the anticancer agents after injection. A desirable distribution condition is that the anticancer agents are confined only inside the tumor for a desirable period of time. The diffusion of anticancer agents inside the tumorous tissues and from tumorous tissue to normal tissue might eventually lead to normal tissue damages. On the other hand, if the viscosity is too high and thus the distribution is too low, the agents would only accumulate at the targeted region and will reduce the clinical effects of the agents. The present disclosure demonstrates that when a pharmaceutical composition containing p-TSA has a viscosity of from 40 to 60 cP, or from 47.2 to 48.4 cP, the injection of that particular agents has desirable distribution and diffusion features, including easy to observe, easy to inject, and leads to a diffusion pattern that helps to release the agents slowly, prolong the reaction period in the region, reduce potential metabolism of the agents by the tissue, and yet not to diffuse too quickly into peripheral tissues that are not the targeted region. The present disclosure also demonstrates that ultrasonic imaging is an auxiliary tool to help doctors to locate a desirable injection site and monitor the diffusion status of p-TSA-containing pharmaceutical composition in a liver intratumoral injection.

It is however understandable to a person having ordinary skill in the art that any pharmaceutical composition containing p-TSA that has a viscosity of from 20 to 200 cP, such as from 40 to 60 cP and from 47.2 to 48.4 cP can exert the desirable distribution patterns in a liver intratumoral injection, and that Sample A is an illustrative example having the desirable viscosity.

The present disclosure further demonstrates that a combination of a pharmaceutical composition containing a benzenesulfonamide derivative with a viscosity of from 20 to 200 cP, such as from 40 to 60 cP and from 47.2 to 48.4 cP and a needling instrument with an 18 G needle exerts a desirable easibility/difficulty to inject the composition intratumorally. Herein incorporated is the definition of a needle with 18 G. An 18 G needle has a nominal outer diameter of 1.270 mm±0.013 mm, a nominal inner diameter of 0.838 mm±0.038 mm and a nominal wall thickness of 0.216 mm±0.013 mm.

The present disclosure shows that when the viscosity of the composition is from 40 to 60 cP and an 18 G needle is used, the operational efficiency (visibility and easibility/difficulty) and the treatment features (mainly diffusion, accumulation and retention of the composition) achieve a desirable balance; whereas, when at 18.2-23.3 cP with a 18 G needle, such desirable balance is broken. Accordingly, the threshold of a desirable balance between operational efficiency and treatment features is located between 23 cP and 40 cP, a difference of 17 cP. It is to be noted that the viscometer uses a calibration standard solution as 500 cP and pure water as 1 cP. The maximal measurement capability is 21800 cP and the minimal is 7 cP. Therefore, a difference of 17 cP is extremely small and might not be further differentiated. Yet, such small difference results in significant difference in the process of injecting the composition to the tissue. Taken together, the present disclosure provides a pharmaceutical composition (P) containing a benzenesulfonamide derivative with a viscosity larger than any value between 23 cP to 40 cP (P≥X where 40 cP≥X≥23 cP) would exert a desirable balance between operational efficiency and treatment features.

Example 3: Viscosity of Toluene Sulfonamide-Containing Pharmaceutical Composition (Formulations PTS-Taiwan and PTS-China)

Two different samples, PTS-Taiwan and PTS-China, were used in this example. Formulation PTS-China contained 30% by weight of p-TSA (Sigma Aldrich), 30% by weight of PEG-400, 15% by weight of 2-ethyl-1,3-hexandiol, 8% by weight of propanediol, 4% by weight of sebacic acid, 5% by weight of DMSO, and 8% by weight of anhydrous ethanol. The constituents of the Formulation PTS-Taiwan were the same as that of Formulation PTS-China, except that p-TSA in the Formulation PTS-Taiwan was synthesized by the inventors. The process of preparing such two samples was described as follows. p-TSA, PEG-400 and 2-ethyl-1,3-hexandiol were mixed in a container and heated to 85° C. to 95° C. with stirring to form Solution A. Sebacic acid and propanediol were mixed in another container and heated to 85° C. to 95° C. with stirring to form Solution B. Solution A and Solution B were then mixed and stirred at 85° C. to 95° C. DMSO and a portion of anhydrous ethanol were mixed and stirred uniformly in a container to form Solution C. The mixture of Solution A and Solution B was cooled to 60° C. and then added with Solution C. The mixture solution was cooled to room temperature and then added with the remaining anhydrous ethanol, followed by being filtered through a membrane filter with the pore size of 0.45 μm to obtain the sample to be tested.

Figure 5:
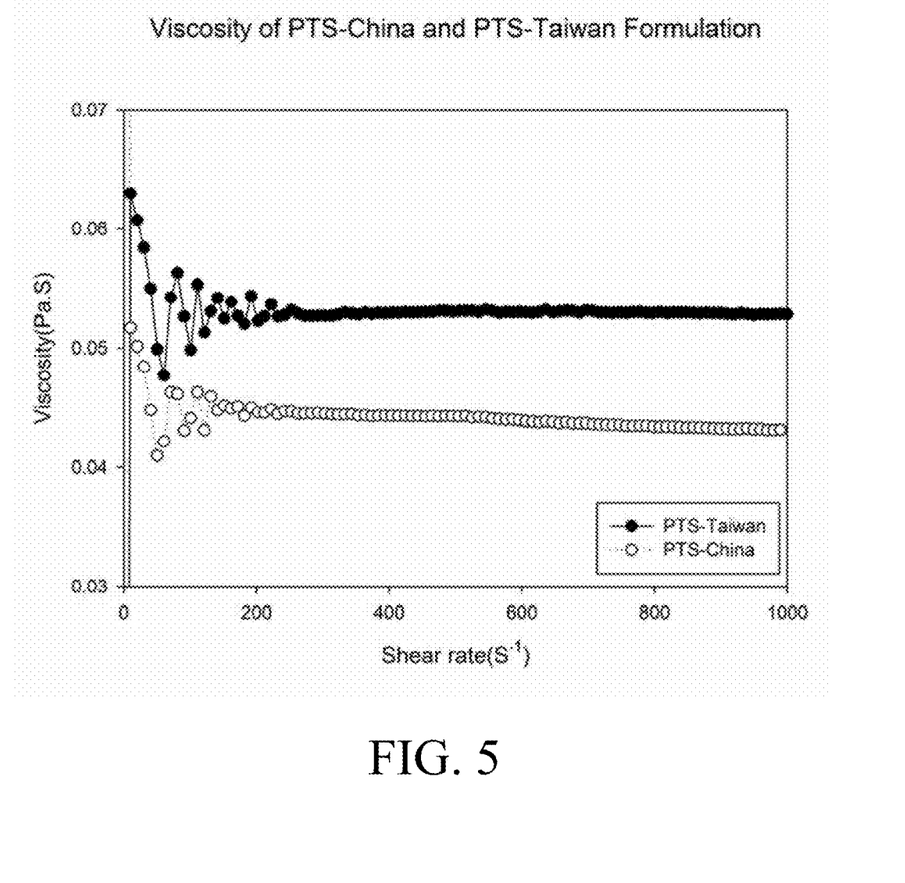
FIG. 5 shows a result of determining viscosities of Formulations PTS-Taiwan and PTS-China (1 centipoise (cP)= 0.001 pascal second (Pa·S)).

For determining viscosity of Formulations PTS-Taiwan and PTS-China, the samples to be tested were kept at 25° C. in a water bath. The rheometer (HAAKE RS-1, Thermo Fisher Scientific Co. Ltd) was set at 25° C., with a shear rate of from 0 (1/s) to 1000 (1/s). After rheometer was calibrated, about 3 mL of the sample was loaded into the sample tank of the rheometer by pipette. The viscosity of the sample was then determined at different shear rates. The sample tank was washed with alcohol and water when the determination was finished. The rheometer would be calibrated again before determining the different sample. The results of determining viscosities of Formulations PTS-Taiwan and PTS-China were shown in FIG. 5.

Example 4: Properties of Pharmaceutical Composition of Benzenesulfonamides (PTS100)

The pharmaceutical composition PTS100 for intratumoral injection administration was a clear, colorless, oily, sterile solution, containing the components as listed in Table 3, and that could be packaged in either 3- or 5-mL glass ampoules. PTS100 contains 330 mg/mL of the active drug p-TSA.

TABLE 3

| Ingredients | Unit Formula (mg/mL) | Unit Formula (g per 3 mL ampoule) | Unit Formula (g Per 5 mL ampoule) |
| --- | --- | --- | --- |
| p-TSA | 330.0 | 0.990 | 1.650 |
| Polyethylene glycol | 335.0 | 1.005 | 1.675 |
| 2-ethyl-1,3-hexanediol | 164.0 | 0.492 | 0.820 |
| Propanediol | 82.0 | 0.246 | 0.410 |
| Dimethyl sulfoxide | 67.0 | 0.201 | 0.335 |
| Sebacic acid | 37.0 | 0.111 | 0.185 |
| Ethanol | To 1.0 mL | To 3.0 mL | To 5.0 mL |

The properties of PTS100 were determined and described as follows.

Light Sensitivity

After had being stored in room temperature and lighting level from 4500 to 5500 Lx environment for 0, 5, 10 days, all PTS100 products displayed no significant change in appearance, particular matter inspection, and p-TSA content analysis. It demonstrated that PTS100 was insensitive to short-term light exposure.

Stability

The stability testing of PTS100 was completed for 24 months at the following storage conditions:

25±2° C., 60±5% relative humidity (RH) and 40±2° C., 75±5% RH

Example 5: Efficacy of TACC Treatment by PTS100 in Clinical Trials

Patient Population

Selected patients were those with non-small cell lung severe malignant airway obstruction as determined based on the following criteria:

age ranged between 18 and 83 years, diagnosed as lung cancer pathologically, over ⅔ occlusion in right or left bronchi, or over ½ occlusion in trachea, which is confirmed by either CT scan, bronchoscopy, MRI, or X-ray imaging.

Enrollment of the Study

The total number of subjects initially planned for inclusion in the study was 89 based on biostatistical validity. The enrollment began with a total of 90 subjects. The total number of TACC in the study was 8 cases.

Administration Method

To patients with central air way non-small cell lung cancer (NSCLC) tumor severe obstruction, PTS100 was administrated via bronchoscopic intratumoral injection. All subjects need to have an outpatient surgery for PTS100 treatment. For each injection, the vital functions of patients will be monitored during therapy and vital sign examination will be confirmed after surgery.

For administration method, 5 mL of PTS100 was aspirated from glass ampoule and mixed adequately with accessorized solvent. After mixing, PTS100 was injected into the tumor slowly by puncture needle. Necrotized tissue was removed by biopsy forceps before each injection. A treatment cycle of PTS100 was 2 weeks, and the injection dose in a treatment cycle was 2 to 3 doses per week. The first treatment cycle must include 4 treatments or more.

The dose of PTS100/ethanol mixture could be 0.1-1.5 mL (equivalent to 0.07-1 mL PTS100), with the maximal dose of 7 mL (5 mL PTS100), tailored to the size of tumor. Maximal cumulative dose of PTS100/ethanol mixture was 14 mL (10 mL PTS100) for any single day. It is to be noted that the number of injection could be based on the range of necrotized tumor, and should be determined to necrotize the whole tumor.

Study Design

Open-label, single arm, non-randomized.

Study Results

This study enrolled 90 subjects; 88 subjects (73 males and 15 females, median age was 57.5 years (range between 22 and 80 years)) were included in the full analysis set (FAS), with 72 subjects completed all study treatment and included in the per protocol set (PPS). Among the 88 cases, 75% was squamous-cell carcinoma, and 12.5% was adenocarcinoma. Out of the patients in the FAS, 52.3% were staged as IV, and 42% were staged as IIIB.

The primary endpoint for the evaluation of the efficacy was based on the objective resolution rate of target tumor, and the improvement of the airway occlusion, as determined by computed tomography (CT) in accordance with Response Evaluation Criteria In Solid Tumors (RECIST) standards and WHO standards, and evaluated on the $7^{th}$ day after the last dose ("concluding visit") and the $30^{th}$ days after concluding visit ("follow-up visit"). The efficacy index of FAS and PPS were summarized in Tables 4 and 5.

TABLE 4

Efficacy analysis of PTS100 injection in NSCLC patients with central airway Obstruction (in FAS)

| | Efficacy Index | Verification method | Concluding visit (the $7^{th}$ day after last dose) | Follow-up visit (the $30^{th}$ day after concluding visit) |
| --- | --- | --- | --- | --- |
| primary | Objective Resolution Rate (CR + PR) | CT RECIST | 59.09% | 43.18% |
| | | Bronchoscopy RECIST | 48.86% | 29.55% |
| | | CT WHO standard | 67.05% | 47.73% |
| | | Bronchoscopy WHO standard | 76.14% | 37.50% |
| | Improvement rate of intratracheal obstruction | CT | 69.41% | 69.12% |
| | | Bronchoscopy | 72.83% | 68.52% |
| Clinical beneficial | Baseline dyspnea index (BDI) | — | 64.77% | 34.09% |
| | Forced vital capacity (FVC) | — | 39.77% | 22.73% |
| | Performance status | ECOG | 34.09% | 25.00% |

CR: complete response.
PR: partial response.

TABLE 5

Efficacy analysis of PTS injection in NSCLC patient with central airway Obstruction (in PPS)

| | Efficacy Index | Verification method | Concluding visit (the 7$^{th}$ day after last dose) | Follow-up visit (the 30$^{th}$ day after concluding visit) |
|---|---|---|---|---|
| primary | Objective Resolution Rate (CR + PR) | CT RECIST | 68.08% | 48.61% |
| | | Bronchoscopy RECIST | 56.94% | 33.33% |
| | | CT WHO standard | 77.78% | 54.17% |
| | | Bronchoscopy WHO standard | 88.89% | 43.06% |
| | Improvement rate of intratracheal obstruction | CT | 70.45% | 70.47% |
| | | Bronchoscopy | 74.09% | 70.64% |
| Clinical beneficial | Baseline dyspnea index (BDI) | — | 76.39% | 38.89% |
| | Forced vital capacity (FVC) | — | 45.83% | 25.00% |
| | Performance status | ECOG | 41.67% | 30.56% |

CR: complete response.
PR: partial response.

TACC Population from NSCLC-Severe MAO Clinical Trial

Among the recruited participants, 8 patients were diagnosed and categorized as TACC. The response rates of the TACC patients were listed in Table 6. The treatment had an over 70% reduction in airway obstruction rate both in 7 days and 30 days post treatment, and also an over 87.5% objective response rate according to Response Evaluation Criteria in Solid Tumor (RECIST) was achieved. In addition, 3-years survival rate of these 8 patients was 100% (8/8 survived) and the 5-year survival rate was 60% (5/8 survived). In spite of the survival rate of these 8 patients is similar to current standard of care, PTS100 injection provides a disease-free margin comparing to other physical treatments to avoid possibilities of future local recurrence and distal metastasis.

TABLE 6

Clinical response of PTS100 treatment on TACC patients

| Patient | | | 7 days post treatment | | | | 30 days follow up | | | | Survival | |
|---|---|---|---|---|---|---|---|---|---|---|---|---|
| | | | Bronchoscopy | | CT | | Bronchoscopy | | CT | | | |
| Subject number/ name | Tumor location | TNM stage | AOR reduction (%) | ORR | AOR reduction (%) | ORR | AOR reduction (%) | ORR | AOR reduction (%) | ORR | Days | Last interview status |
| 01001 ZWH | LMB | T4N2MX IIIb | 81.9 | PR | 100.0 | CR | 93.1 | PR | 100.0 | CR | 619 | Alive |
| 01005 CWJ | ET | T4NM1 IV | 78.5 | PR | 56.7 | PR | 95.2 | PR | 68.5 | PR | 532 | Alive |
| 01019 CPM | LMB | T4N3M1 IV | 85.6 | PR | 100.0 | CR | LFU | LFU | LFU | LFU | 120 | Alive |
| 06001 LSZ | UST | T4N0M0 IIIb | 69.6 | PR | 84.8 | PR | 65.6 | PR | 71.5 | PR | 424 | Alive |
| 07011 SYH | RMB | T3N0M1 IV | 81.4 | PR | 100.0 | CR | 84.9 | PR | 100.0 | CR | 172 | Alive |
| 17008 QXM | MST | T4N0MX IIIb | 88.7 | PR | 51.1 | SD | 74.5 | PR | 18.0 | PR | 397 | Alive |
| 17010 DMC | LST | T4N0MX IIIb | 94.6 | PR | 93.8 | PR | 96.3 | PR | 87.3 | PR | 763 | Alive |
| 17011 YWH | MST | T4N0MX IIIb | 81.9 | PR | 53.8 | PR | 93.1 | PR | 59.1 | PR | 800 | Alive |
| ORR (%) | | | 72.5 | 100.0 | 80.0 | 87.5 | 72.8 | 100.0 | 72.0 | 100.0 | 457 | All alive |

AOR: airway obstruction rate.
LFU: lost in follow up.
LMB: left main bronchus.
ET: end of trachea.
UST: upper section of trachea.
RMB: right main bronchus.
MST: middle section of trachea.
LST: lower section of trachea.
ORR: objective response (RECIST).
CR: complete response.
PR: partial response.
SD: stable disease.

Among the 8 patients with TACC, two patients were lost follow-up at the last visit, so the efficacy of 6 TACC patients was listed in Table 7, for comparing with the efficacy of other patients suffering from squamous carcinoma or adenocarcinoma.

TABLE 7

Tracheal adenoid cystic carcinoma in PTS100 Phase III clinical trial

| Pathological sun-types | AOR by bronchoscopy (RECIST criteria) | Patient Number | Percentage |
|---|---|---|---|
| Tracheal Adenoid Cystic Carcinoma (n = 6) | CR | 2 | 33.3% |
|  | PR | 4 | 66.7% |
|  | CR + PR | 6 | 100.0% |
| Squamous Carcinoma (n = 35) | CR | 13 | 37.1% |
|  | PR | 15 | 42.9% |
|  | CR + PR | 28 | 80.0% |
| Adenocarcinoma (n = 7) | CR | 5 | 71.4% |
|  | PR | 0 | 0 |
|  | CR + PR | 5 | 71.4% |

Note:
RECIST criteria evaluation was based on the F1 comparison of visit sequence 1 & 6 (screening & visit after day 30 of dosing).

The results showed that the pharmaceutical composition of the present disclosure exhibits different efficacies for the different types of tumor. In comparison to the treatment of squamous carcinoma or adenocarcinoma, the pharmaceutical composition of the present disclosure is more effective for the treatment of TACC. Therefore, the pharmaceutical composition of the present disclosure can treat cancer, especially TACC, and improve the life quality and clinical symptoms such as MAO of the patients. No significant increase in adverse reactions was found.

The disclosure has been described using exemplary preferred embodiments. However, it is to be understood that the scope of the disclosure is not limited to the disclosed embodiments. On the contrary, it is intended to cover various modifications and similar rearrangement. The scope of the claims therefore should be accorded the broadest interpretation so as to encompass all such modifications and similar arrangements.

What is claimed is:

1. A method for treating adenoid cystic carcinoma, comprising administering a therapeutically effective amount of a pharmaceutical composition to a subject in need thereof, wherein the pharmaceutical composition comprises a benzenesulfonamide derivative or a pharmaceutically acceptable salt thereof, and a pharmaceutically acceptable carrier, wherein the benzenesulfonamide derivative is represented by formula (I):

or a pharmaceutically acceptable salt thereof,
wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring, and
wherein the alkyl, alkoxy, cycloalkyl, cycloheteroalkyl groups and the ring are unsubstituted or substituted with one or more substituents.

2. The method of claim 1, wherein the substituent is selected from the group consisting of phenyl, halo, oxo, ether, hydroxyl, carboxyl, amino, sulfo and sulfonamide group.

3. The method of claim 1, wherein the benzenesulfonamide derivative or the pharmaceutically acceptable salt thereof is at least one selected from the group consisting of para-toluene sulfonamide, ortho-toluene sulfonamide, meta-toluene sulfonamide, N-ethyl ortho-toluene sulfonamide, N-ethyl para-toluene sulfonamide, N-cyclohexyl para-toluene sulfonamide,

-continued

-continued

-continued

4. The method of claim 1, wherein the pharmaceutical composition has a viscosity of from 20 to 200 cP.

5. The method of claim 4, wherein the pharmaceutical composition has the viscosity of from 40 to 60 cP.

6. The method of claim 5, wherein the pharmaceutical composition has the viscosity of from 47.2 to 48.4 cP.

7. The method of claim 1, wherein the pharmaceutically acceptable carriers are selected from the group consisting of polyethylene glycol (PEG), alkylene glycol, sebacic acid, dimethyl sulfoxide (DMSO), alcohol and a combination thereof.

8. The method of claim 7, wherein the alkylene glycol is at least one of 2-ethyl-1,3-hexandiol and propanediol.

9. The method of claim 1, wherein the benzenesulfonamide derivatives are present in an amount of from 10% to 50% by weight.

10. The method of claim 9, wherein the benzenesulfonamide derivatives are present in an amount of from 20% to 40% by weight.

11. The method of claim 9, wherein the pharmaceutical composition further comprises at least one of 20% to 50% by weight of PEG, 5% to 15% by weight of propanediol, 1% to 5% by weight of sebacic acid, 10% to 20% by weight of 2-ethyl-1,3-hexanediol, 5% to 10% by weight of dimethyl sulfoxide and anhydrous ethanol in a range of from 0%, not included, to 30% by weight.

12. The method of claim 11, wherein the pharmaceutical composition comprises the benezesulfonamide derivatives in an amount of about 33% by weight, the PEG in an amount of about 35.5% by weight, the 2-ethyl-1,3-hexandiol in an amount of about 16.4% by weight, the propanediol in an amount of about 8.2% by weight, the sebacic acid in an amount of about 3.7% by weight, and the DMSO in an amount of about 6.7% by weight.

13. The method of claim 1, wherein the pharmaceutical composition is administered to the subject intratumorally, intravenously, subcutaneously, intradermally, intrathecally, intraperitoneally, intramuscularly, or intrapleuraly.

14. The method of claim 13, wherein the pharmaceutical composition is administered to the subject by a needling instrument having an 18G needle.

15. The method of claim 1, wherein the adenoid cystic carcinoma is tracheal adenoid cystic carcinoma.

16. The method of claim 1, wherein the benzenesulfonamide derivatives in the pharmaceutical composition is administered to the subject in a therapeutically effective amount of from about 1000 mg to about 3300 mg per day.

17. The method of claim 1, wherein the pharmaceutical composition is administered to the subject 1 to 4 times per week.

18. The method of claim 1, wherein the pharmaceutical composition is administered to the subject for a 1- to 3-week treatment period.

19. The method of claim 1, wherein the benzenesulfonamide derivatives in the pharmaceutical composition is administered to the subject in a therapeutically effective amount of from about 23 mg to about 3300 mg per day.

20. A method for treating adenoid cystic carcinoma, comprising administering a therapeutically effective amount of a pharmaceutical composition to a subject in need thereof, wherein the pharmaceutical composition comprises a benzenesulfonamide derivative or a pharmaceutically acceptable salt thereof, and a pharmaceutically acceptable carrier, wherein the benzenesulfonamide derivative or the pharmaceutically acceptable salt thereof is at least one selected from the group consisting of:

* * * * *